US010180403B1

(12) United States Patent
Safai et al.

(10) Patent No.: US 10,180,403 B1
(45) Date of Patent: Jan. 15, 2019

(54) SHEAROGRAPHY FOR SUB MICROCELLULAR SUBSTRATE NONDESTRUCTIVE INSPECTION

(71) Applicant: The Boeing Company, Chicago, IL (US)

(72) Inventors: Morteza Safai, Newcastle, WA (US); Xiaoxi Wang, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/629,638

(22) Filed: Jun. 21, 2017

(51) Int. Cl.
*G01B 9/02* (2006.01)
*G01N 21/956* (2006.01)

(52) U.S. Cl.
CPC ....... *G01N 21/956* (2013.01); *G01B 9/02094* (2013.01); *G01N 2201/06113* (2013.01)

(58) Field of Classification Search
CPC ....... G01N 21/956; G01N 2201/06113; G01B 9/02094; G01B 9/02095; G01B 9/02097; G01B 9/02098; G01B 11/16; G01B 11/161; G01B 11/162; G01J 2009/0215; G01J 9/0215
USPC .......................................................... 356/520
See application file for complete search history.

(56) References Cited

U.S. PATENT DOCUMENTS

| | | | |
|---|---|---|---|
| 5,257,088 A | 10/1993 | Tyson et al. | |
| 5,481,356 A * | 1/1996 | Pouet | G01B 11/162 356/35.5 |
| 5,786,533 A * | 7/1998 | Newman | G01B 9/025 73/146 |
| 6,246,483 B1 * | 6/2001 | Smith | G01B 11/162 356/35.5 |
| 6,717,681 B1 | 4/2004 | Bard et al. | |
| 2001/0040682 A1 | 11/2001 | Lindsay et al. | |
| 2004/0212795 A1 * | 10/2004 | Steinbichler | G01B 11/162 356/35.5 |
| 2005/0264796 A1 * | 12/2005 | Shaw | G01B 11/162 356/237.2 |

(Continued)

FOREIGN PATENT DOCUMENTS

| | | |
|---|---|---|
| EP | 1061332 A2 | 12/2000 |
| WO | 2006/001712 A2 | 1/2006 |

OTHER PUBLICATIONS

Burleigh, D., et al., "Laser Shearographic Testing of Foam Insulation on Cryogenic Fuel Tanks", Review of Progress in Quantitative Nondestructive Evaluation, vol. 12, 1993, pp. 411-418.

(Continued)

*Primary Examiner* — Tarifur R Chowdhury
*Assistant Examiner* — Jonathon Cook
(74) *Attorney, Agent, or Firm* — MH2 Technology Law Group LLP (57) ABSTRACT

Provided is a method and system for dynamic shearographic inspection. The dynamic shearographic method allows nondestructive inspection of layered materials, in particular, those including a porous material. The method uses a load profile that increases and decreases the load, for example in a saw-tooth manner, without decreasing the load back down to the initial loading state, usually zero loading. Using the load profile in this manner constantly refreshes the reference speckle images to minimize background noise and allows defects to be distinguished from the noise.

19 Claims, 5 Drawing Sheets

(56) References Cited

U.S. PATENT DOCUMENTS

2008/0295579 A1 12/2008 Safai et al.
2016/0209205 A1* 7/2016 Enevoldsen ......... G01B 11/162

OTHER PUBLICATIONS

Davis, C. et al., "Shearographic Non-Destructive Evaluation of Space Shuttle Thermal Protection Systems", 1995, 12 pages.
Lee, J., et al., "Application of grating shearography and speckle shearography to mechanical analysis of composite material", Composites: Part A, vol. 35, 2004, pp. 965-976.
Joenathan, C. et al., "Speckle interferometry with temporal phase evaluation for measuring large-object deformation", Applied Optics, vol. 37, No. 13, May 1, 1998, pp. 2608-2614.
Unknown, "High-Speed Dispensing Valve", TLX Technologies: Innovative Electromagnetic Solutions, 2008, 1 page.
Specification and drawings in co-pending U.S. Appl. No. 15/629,673, 44 pages.
Extended European Search Report dated Nov. 2, 2018 in corresponding European Application No. 18178451.3, 13 pages.

* cited by examiner

SHEAROGRAPHY FOR SUB MICROCELLULAR SUBSTRATE NONDESTRUCTIVE INSPECTION

FIELD

The present disclosure generally relates to methods and systems for nondestructive inspection.

BACKGROUND

Figure 1A:
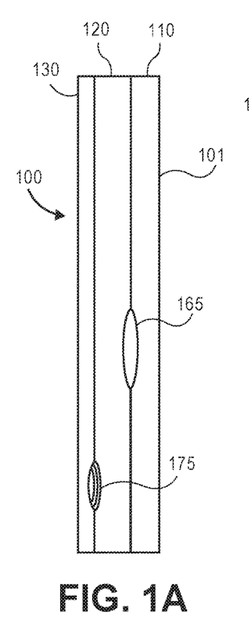
FIGS. 1A-B depict a layered composite material with defects in a loaded and unloaded state.
Figure 1B:
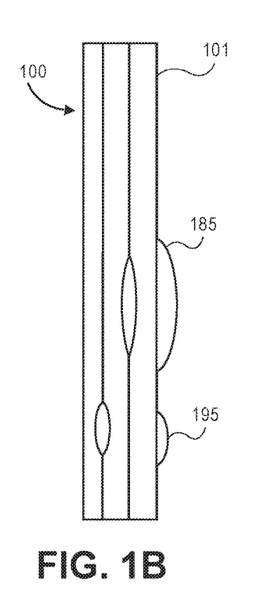
Figure 1C:
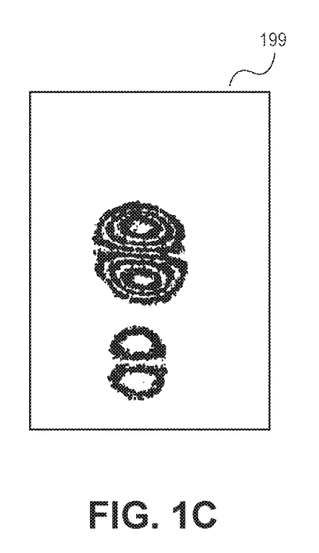
FIG. 1C schematically depicts a speckle pattern showing the out-of-plane deformation resulting from shearographic inspection.

Shearography is method for nondestructive inspection used to detect surface deformation. It is conducted by illuminating a surface of a test object using laser light. An image of the illuminated surface is captured and sheared to produce an interference or "speckle" pattern. Another speckle pattern is then captured while the surface of the test object is subject to a small load, for example, caused by vacuum, vibration, or heat. Because shearography detects out of plane deformation, it is particularly useful for inspecting layered materials for defects underlying the surface such as delamination. FIG. 1A depicts a layered material 100 formed of three layers 110, 120, and 130. A delamination 165 exists between layers 110 and 120. And, another delamination 175 exists between layers 120 and 130. When no load is applied to a top surface 101 of layered material 100, there is little or no out of plane deformation. In contrast, FIG. 1B depicts out of plane deformation 185 and 195 corresponding to delaminations 165 and 175, respectively, when top surface 101 of layered material 100 is subject to loading by vacuum, heat, or mechanical methods. As depicted in a shearographic image 199 in FIG. 1C, this method detects the out-of-plane deformation caused by delaminations 165 and 175 by subtracting a speckle pattern of top surface 101 of layered material 100 in the unloaded state from the speckle pattern of top surface 101 in the loaded state.

Figure 1D:
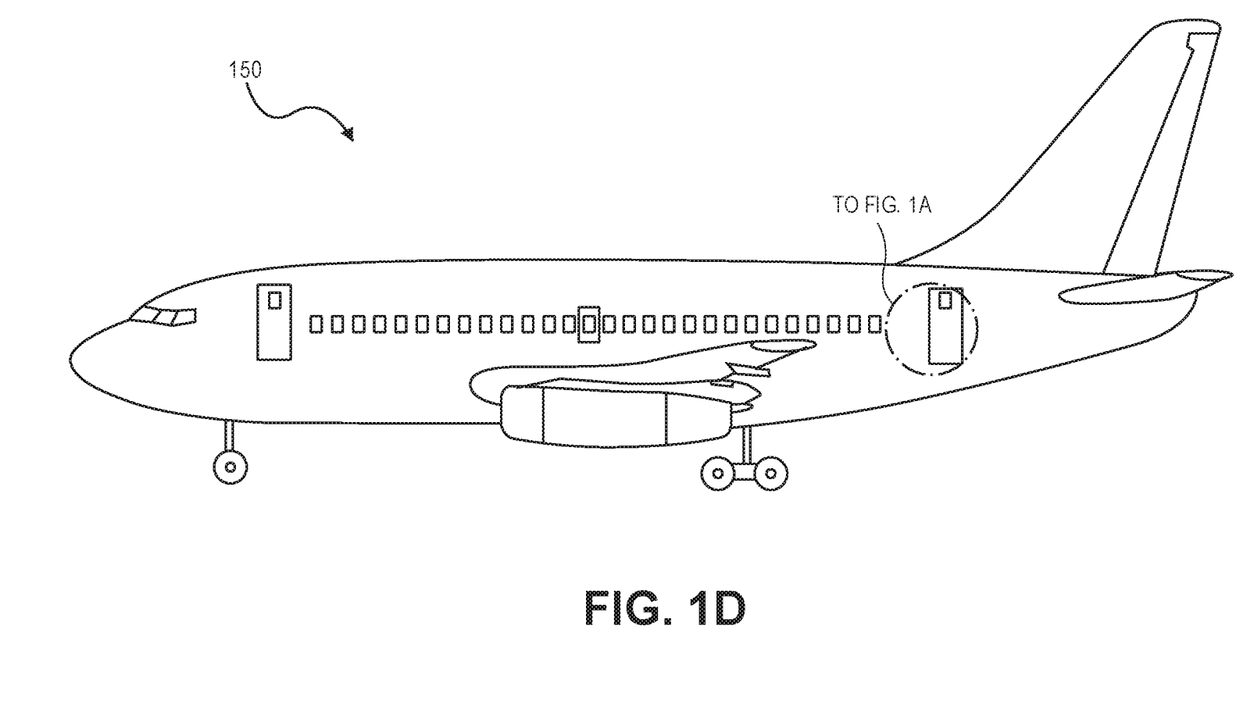
FIG. 1D depicts an aircraft including an interior having layered composite materials.

Materials used for interiors of aircraft and other vehicles are subject to demanding performance requirements including high strength to weight ratio, mechanical strength, and dimensional stability. Low heat, smoke, and toxin release in case of fire are also desirable. To meet these requirements, layered composite materials, such as multi-layered laminate materials, are often used. FIG. 1D shows an exemplary vehicle, aircraft 150 including an interior having a layered composite material, for example, as shown in FIG. 1A. In this case, layer 110 represents a common material used for the visible surfaces of aircraft interiors known as decorative laminate or "declam." Declam generally includes one or more polymer layers and one or more adhesive layers. Declam typically resides over a panel skin, for example layer 120 in FIG. 1A, and is formed of one or more prepreg adhesive layers. The panel skin in-turn resides over a honeycomb core, for example layer 130, in FIG. 1A. Inspecting layered composite materials, such as declam covered areas, for defects during production of an aircraft and while the aircraft is in service presents several challenges including access to only the visible surfaces, large amounts of surfaces to inspect, and the desirability of a nondestructive method.

To date, use of shearography to inspect declam-covered areas has seen limited success due to the porous nature of the honeycomb core. Because defects can be the same size or smaller than the pores, conventional methods for shearographic inspection suffer from an inability to distinguish defects from noise caused by the porous materials (e.g., decorrelation noise or "D-Noise"). Thus, a need exists in the industry to address the aforementioned deficiencies and inadequacies.

SUMMARY

According to the present teachings, a shearographic inspection method for detecting defects is provided. The method includes illuminating a top surface of a test piece with a coherent light and capturing a first shearographic image that includes a first speckle pattern, while zero vacuum pressure is being applied to the top surface. A first vacuum pressure is applied to the top surface and a second shearographic image is captured during the applying of the first vacuum pressure to the top surface. The second shearographic image includes a second speckle pattern. The first speckle pattern and the second speckle pattern are then used to determine whether a defect exists. The vacuum pressure at the top surface is then reduced and a second vacuum pressure is applied to the top surface, wherein the second vacuum pressure is less than the first vacuum pressure and greater than zero vacuum pressure. According to the present teachings, a shearographic inspection method can further include a third shearographic image that can be captured during the applying of the second vacuum pressure to the top surface, wherein the third shearographic image includes a third speckle pattern. Vacuum pressure at the top surface can be increased and a third vacuum pressure can be applied to the top surface, wherein the third vacuum pressure is greater than the first vacuum pressure. A fourth shearographic image can be captured during the applying of the third vacuum pressure. The fourth shearographic image includes a fourth speckle pattern. Using the third speckle pattern and the fourth speckle pattern existence of a defect in the test piece can be determined.

According to the present teachings, a nondestructive method for detecting defects in a multi-layered laminate is provided. In the method, a top surface of the multi-layered laminate is illuminated with a coherent light. A first reference speckle image of the top surface of the multi-layered laminate is then obtained, wherein the top surface is subject to a first vacuum pressure and the first vacuum pressure is 0 or greater during the obtaining of the first reference speckle image. A second vacuum pressure is applied to the top surface while capturing a first test speckle image of the top surface, wherein the second vacuum pressure is greater than the first vacuum pressure. The vacuum pressure at the top surface is then reduced to a third vacuum pressure, wherein the third vacuum pressure is less than the second vacuum pressure and greater than the first vacuum pressure. A second reference speckle image of the top surface is obtained while applying the third vacuum pressure to the top surface. The vacuum pressure at the top surface is then increased to a fourth vacuum pressure, wherein the fourth vacuum pressure is greater than the second vacuum pressure. A second test speckle image of the top surface is obtained while applying the fourth vacuum pressure to the top surface. The second reference speckle image and the second test speckle image are then used to determine whether a defect exists in the multi-layered laminate.

According to the present teachings, a shearographic inspection system is provided. The system includes a coherent light source configured to provide a coherent beam of light, one or more optical elements to expand the coherent beam of light and direct the expanded coherent beam of light to illuminate a top surface of a test piece, a shearography camera to capture speckle images of the illuminated top surface of the test piece, and a loading system configured to increase and decrease a load to the top surface of the test piece. The shearographic inspection system also includes an image manipulation system to manipulate speckle images of the illuminated top surface of the test piece.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate the present disclosure and together with the description, serve to explain the principles of the present disclosure.

DESCRIPTION

Reference will now be made in detail to exemplary implementations of the present disclosure, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary implementations in which the present disclosure may be practiced. These implementations are described in sufficient detail to enable those skilled in the art to practice the present disclosure and it is to be understood that other implementations may be utilized and that changes may be made without departing from the scope of the present disclosure. The following description is, therefore, merely exemplary.

Implementations of the present disclosure address the need for a method to nondestructively inspect layered materials, in particular, those including a porous material layer. The disclosed dynamic shearographic method utilizes a load profile to constantly refresh reference images to minimize background noise. In this method, the load can be increased and decreased, for example in a saw-tooth manner, without decreasing the load back down to the initial loading state, usually zero. This allows defects to be distinguished from decorrelation noise, for example, generated from one or more porous layers of the layered material. Detectable defects include, but are not limited to, disbands, delamination, cracks, and impact damage. The disclosed dynamic shearographic method can be used without the need to know the general location of the defect. Moreover, the disclosed method may be advantageously automated. While the examples below provide methods for detection of defects that overcome the presence of decorrelation noise due to a porous layer, after reading this disclosure, one of ordinary skill in the art will understand that the exemplary methods can be used on materials without a porous layers and on non-layered materials.

Figure 2:
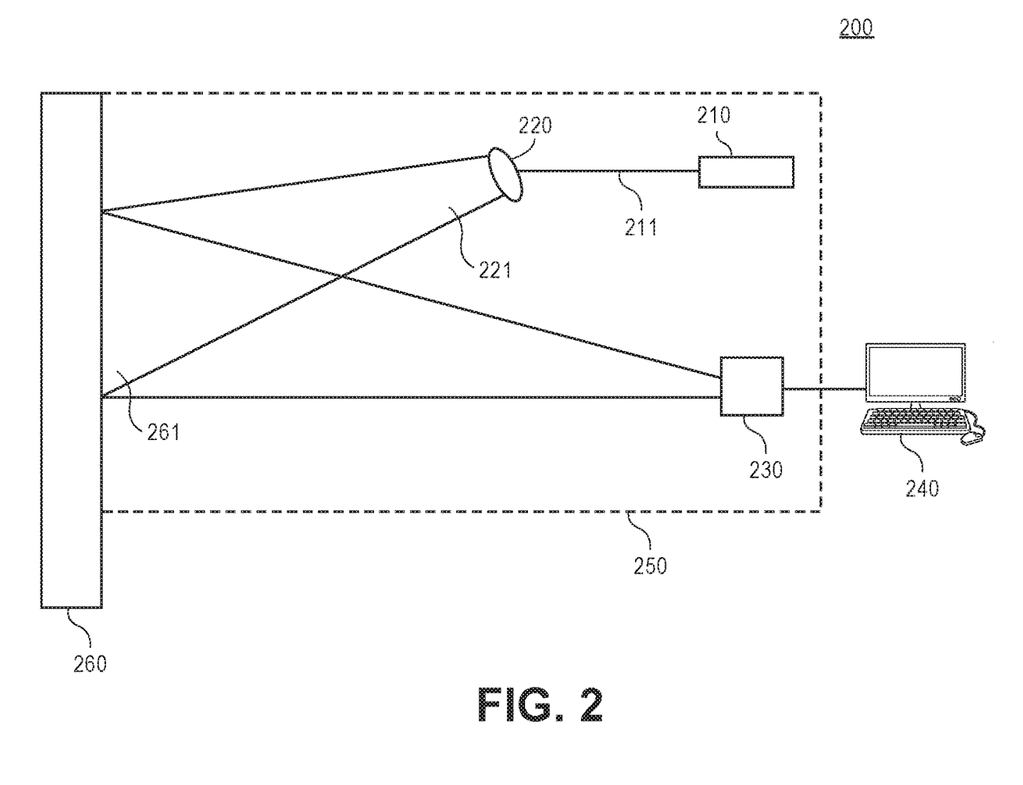
FIG. 2 depicts an exemplary shearographic inspection system according to the present disclosure.

FIG. 2 shows an exemplary shearographic inspection system 200. Shearographic inspection system 200 can include a coherent light source 210, such as a laser or any other source that provides a coherent beam of light 211. As used herein, the terms coherent light or coherent beam refers to light having the same wavelength and phase, generally from a point source, such as a laser. System 200 further includes a beam expander 220 or other optical elements that can expand and direct coherent beam of light 211 towards a test piece 260 to be inspected. A shearography camera 230 captures an image of a speckle pattern on illuminated top surface 261. The term "speckle pattern" is used interchangeably herein with the term "speckle image," which is embedded in a shearographic image.

One of ordinary skill in the art will understand that shearography camera 230 can include a charge coupled device ("CCD") image sensor, lenses and/or other optical elements, and an image shearing device. The image shearing device can be, for example, a prism and a polarizer to produce a pair of laterally displaced ("sheared") images. The shearography camera provides several functions. It receives an image reflected from the test object and produces a pair of laterally displaced, non-parallel images scattered from two different object points that are nearly collinear using the prism. The polarizer allows the two sheared images to interfere with each other to produce the speckle pattern in the shearographic image. Shearography camera 230 also captures the shearographic image, including the embedded speckle pattern, using the CCD sensor. Examples of shearography camera 230 include the Digital Shearography Camera Model VH-5200 VG manufactured by Laser Technology, Inc. (Norristown, Pa.).

Shearographic inspection system 200 can also include a computer 240 with an image manipulation system, for example, software to manipulate the captured images. Examples of imaging software include NI Vision from National Instruments (Austin, Tex.) and Imaging Processing Toolbox from Mathworks (Natick, Mass.). One of ordinary skill in the art will understand that other components may be included in system 200. For example beam splitters, lenses, mirrors, and other optical elements can be used to expand, direct, and collect the coherent light and other software/devices can be used to capture, manipulate, and display the speckle patterns and shearographic images.

The exemplary shearographic inspection system 200 can further include a loading system to load the test piece. The loading system or loading components can load the test piece using pressure, heat, and/or mechanical load. It should be understood that different loading systems can be used for specific inspection situations. The type of loading and loading system selected can depend on a number of factors including the composition of the test piece, the size of the defects, and the size of the area to be inspected. For example, in certain situations a vacuum system can be advantageous for inspecting porous composite materials while heat or acoustic loading can be used to inspect non-porous composite materials. FIG. 2 depicts an exemplary vacuum system 250 that encloses a portion of test piece 260. In exemplary embodiments, vacuum system 250 can enclose some or all of the other components of the shearographic inspection system. Vacuum system 250 can apply a vacuum to test piece 260 to provide a loaded and unloaded condition.

For example, vacuum system 250 can apply a series of vacuum pressures at a rapid cycle rate, for example, a frequency of 60 Hz or more.

In general, shearographic inspection system 200 operates as follows. Coherent light source 210, e.g., a laser, provides a coherent beam of light 211 that is expanded by beam expander 220. An expanded coherent light 221 emerges from beam expander 220 and is directed to illuminate a top surface 261 of the portion of test piece 260 that is enclosed within vacuum system 250. Test piece 260 is also referred to herein as a work piece or test object. Test piece 260 can be any material formed of one or more layers. Examples include, but are not limited to, multi-ply tires, decorative lamination, foam insulation, and thermal protection systems (TPS). Illuminated top surface 261 can be imaged by shearography camera 230. The resultant speckle image can serve as a reference speckle image. Once the reference speckle image is captured, vacuum system 250 can apply a vacuum that loads top surface 261 of test piece 260. A test speckle image can be captured by shearography camera 230. Computer 240 with imaging software can then compare the reference speckle image to the test speckle image. The presence of a defect can then be determined by comparing the test speckle image with the reference speckle image. For example, the reference speckle image can be subtracted from the test speckle image and an operator/technician can then view the subtracted image to determine if a defect is present. Additionally, the images can be further processed, for example, by filtering, prior to viewing by an operator/technician, to make the defects easier to distinguish. In other exemplary embodiments, judgement of an operator/technician can be removed by using defect recognition software to determine the presence of a defect.

Figure 3:
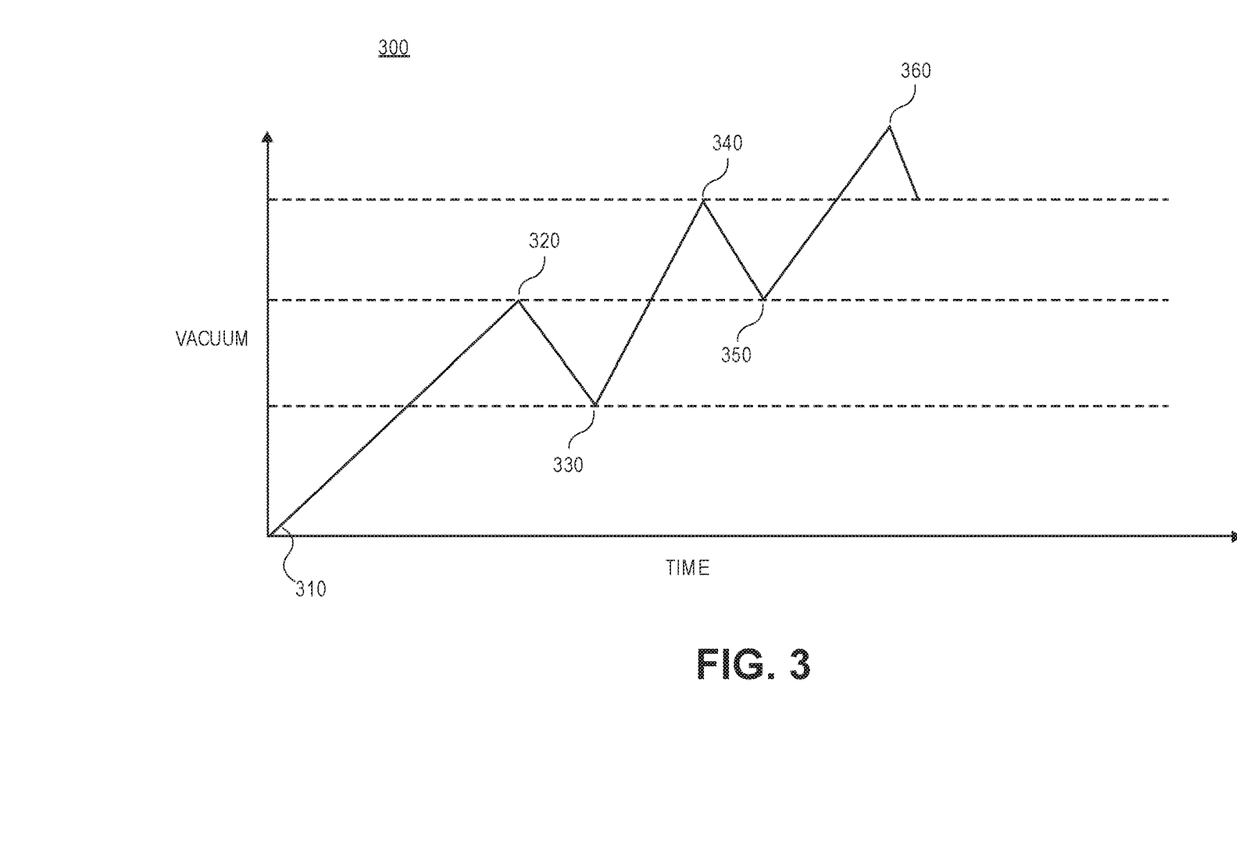
FIG. 3 depicts an exemplary shearographic inspection method according to the present disclosure.

FIG. 3 shows an exemplary dynamic shearographic method 300 for inspecting composite layered materials according to the present disclosure in which the vacuum pressure can be increased and decreased in a saw tooth pattern, for example a linearly increasing saw tooth pattern. As evident from the FIGS, increasing the vacuum pressure refers to a higher vacuum pressure than the vacuum pressure at which the previous speckle image was captured. Similarly, decreasing the vacuum pressure refers to a lower vacuum pressure than the vacuum pressure at which the previous speckle image was captured. FIG. 3 depicts method 300 in terms of vacuum pressure being applied with respect to time during inspection. At 310, no vacuum is being applied so no load is being exerted on the top surface of the test piece. This is also referred to herein as a zero load state. The zero load state can be, for example, atmospheric pressure, e.g., ambient pressure or atmospheric pressure at sea level. A first reference speckle image of the top surface of the test piece is captured at this state. A vacuum is then applied to the test piece and, at 320, a first test speckle image is captured at a first vacuum pressure. At this point, the computer can compare the first reference speckle image to the first test speckle image to determine if a defect is present. One of ordinary skill in the art will understand that a non-automated procedure can also be applied in which an operator can view the first reference speckle image subtracted from the first test speckle image and determine whether a defect is present The vacuum pressure can be decreased to a second vacuum pressure as shown at 330. This second vacuum pressure can be a fraction of the first vacuum pressure, for example, one half, one third, one fourth, etc. of the first pressure, but should be of a higher vacuum pressure than the initial state, e.g., zero vacuum pressure, and less than the first vacuum pressure. The fraction should be less than 1. A second reference speckle image can then be captured at the second vacuum pressure.

At 340, the vacuum pressure can then be increased to a third vacuum pressure that is greater than the first vacuum pressure. A second test speckle image of the top surface of the test piece can be captured at the third vacuum pressure. The computer or operator can then use the second reference speckle image and the second test speckle image to determine if a defect is present. If a defect is detected, the test can be stopped and inspection completed.

If no defect is detected and completion of the inspection does not occur, the vacuum pressure can be decreased to fourth vacuum pressure as shown at 350. Fourth vacuum pressure at 350 can be a fraction of the third vacuum pressure at 340, for example, one half, one third, one fourth, etc., but greater than zero vacuum pressure. In certain exemplary methods, it can be the same fraction as second vacuum pressure is to first vacuum pressure. In other words, if the second vacuum pressure is one half of the first vacuum pressure, then the fourth vacuum pressure can be one half of the third vacuum pressure. In other examples, the second vacuum pressure can be a delta between the initial state (no load) and the first vacuum pressure. The fourth vacuum pressure can be the same delta between the second and third vacuum pressures. For example, if the second vacuum pressure is the mid-point between the initial no load state and the first vacuum pressure, then the fourth vacuum pressure can be the midpoint between the second and third vacuum pressures. A third reference speckle image can then be captured at the fourth vacuum pressure.

The vacuum pressure can then be increased to fifth vacuum pressure at 360. The fifth vacuum pressure at 360 is greater than the third vacuum pressure. A third test speckle image of the top surface of the test piece can be captured. The computer or operator can then use the third reference speckle image and the third test speckle image to determine if a defect is present. If a defect is detected, the test can be stopped.

If a defect is not detected, the increase and decrease of vacuum pressure and the capturing of reference and test speckle images in the manner described herein can be repeated. For example, the exemplary method 300 can continue until the highest vacuum pressure reaches about 5 psi. The exemplary method 300 can continue until the defect in the captured speckle images are discernable from the D-Noise. It is to be understood that FIG. 3 does not depict time in absolute values, but rather in a relative manner. Although depicted as points in FIG. 3, the vacuum pressures at 330 and 350, for example, can be held steady over a period of time so that reference images can be obtained. Similarly, vacuum pressures at 320, 330, and 360 can be held steady for a period of time so the test images can be obtained and determination of a defect can be conducted prior to ending or continuing the inspection. In other words, the vacuum pressure can be increased and decreased, without ever decreasing the vacuum pressure back to the initial state (e.g. atmospheric or ambient pressure), however, the vacuum pressure can be held steady for a period of time so speckle images can be obtained, for example at peaks 320, 340, and 360 and valleys 330 and 350 shown in FIG. 3.

Alternatively, the dynamic shearographic inspection can begin with an initial load being applied to the top surface of the test piece at 310. In this case, the initial load represents the vacuum pressure below which the vacuum pressure does not drop. For example, as shown in FIG. 3, the vacuum pressures at 320, 330, 340, 350, and 360 never equal or drop below the initial vacuum pressure at 310 during the inspection. Because the vacuum pressure is never decreased back to zero or below the vacuum pressure at which the first reference image is captured at 310, the reference speckle images are constantly refreshed to minimize the D-Noise.

The disclosed dynamic shearographic method allows detection of defects, in particular, in layered composite materials that include a microcellular foam layer. As disclosed herein, the applied load (e.g., vacuum pressure) is increased and decreased without returning to the zero or initial state of loading. At the first increased load, for example at 320, the pores of the microcellular layer expand as does the defect. If the signal from the expanded pores (e.g., D-noise) masks the signal from the expanded defect, the defect may not be detected. When the load is decreased to obtain another reference image, for example at 330 and 350, the expansion of the pores and defect lessen, but never return to their initial unexpanded state. As the load is further increased, for example at 340 and 360, eventually the pores will no longer expand further, while the defect continues to expand. At this point, the signal from the defect overcomes the noise from the pores so that comparison of the test and reference images shows the defect.

Figure 4:
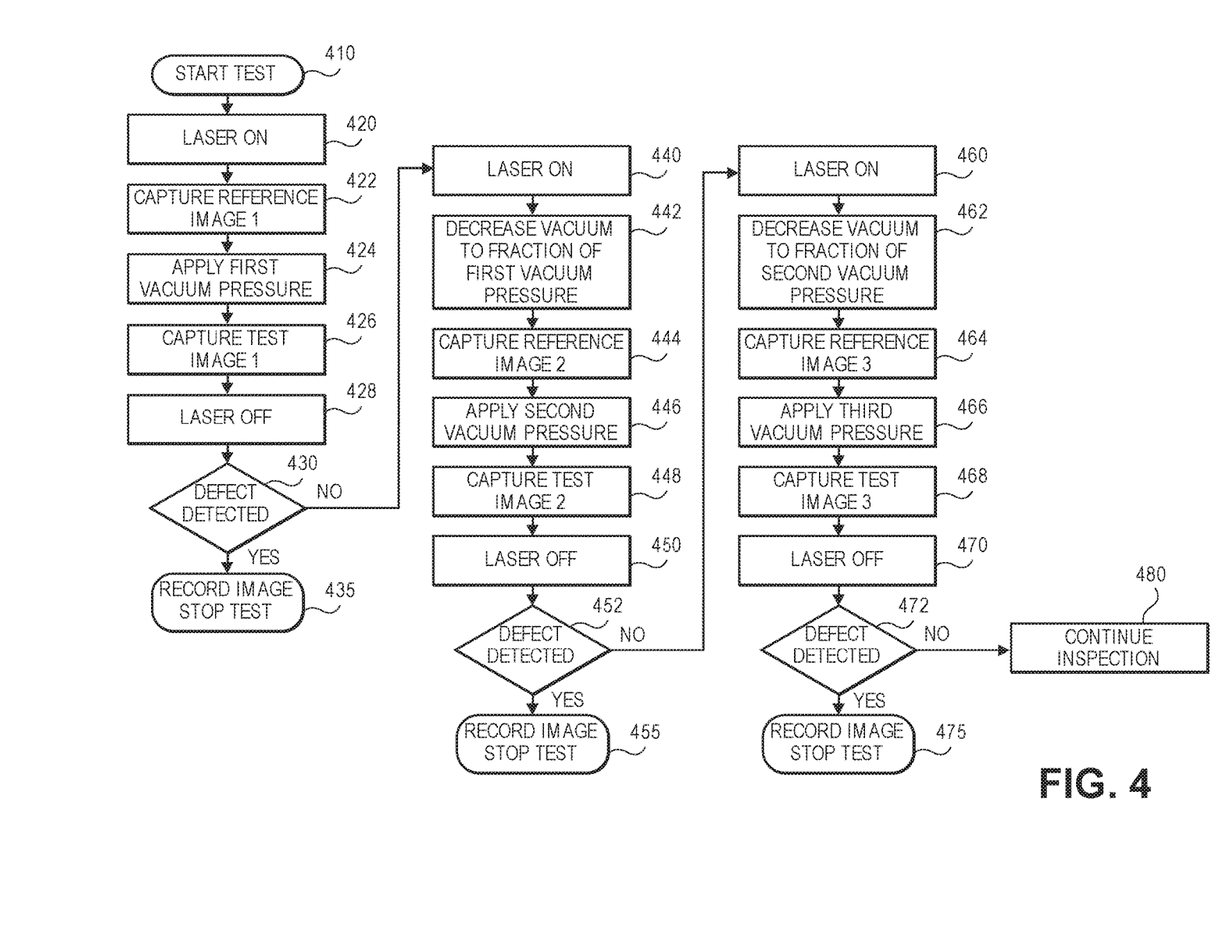
FIG. 4 depicts an exemplary shearographic inspection method syncing application of vacuum pressure and laser light according to the present disclosure.

FIG. 4 depicts syncing of the vacuum pressure and the illumination of the test piece by the laser in dynamic shearographic method 300. By syncing one or both of the vacuum pressure and the laser, the noise can be reduced or even eliminated allowing more accurate detection of a defect. At 410, the test piece can be placed in the vacuum system so that a portion of top surface of the test piece is within the vacuum system and the inspection started. At 420, the laser can be turned on and the portion of the top surface of the test piece illuminated. A first reference image is captured at 422.

At 424, a first vacuum pressure is applied and a first test image is captured at 426. The laser is then turned off at 428. The computer with imaging software uses the first test image and the first reference image to determine whether a defect is detected as shown at 430. If a defect is detected, the inspection can optionally be stopped at 435.

If a defect is not detected, inspection can continue at 440 by turning the laser on. The vacuum pressure can then be decreased to a fraction of the first vacuum pressure, but greater than zero vacuum pressure at 442. In other examples, the vacuum pressure can be reduced to a delta pressure between the initial state and the first vacuum pressure, for example, the mid-point between the two pressures. A second reference image is captured at 444.

At 446, the vacuum pressure is increased to a second vacuum pressure that is higher than the first vacuum pressure. A second test image is captured at 448 and the laser is then turned off at 450. The computer with imaging software can then use the second test image and the second reference image to determine whether a defect is detected as shown at 450. If a defect is detected, the inspection can optionally be stopped at 455.

If a defect is not detected, inspection can continue at 460 by turning the laser on. The vacuum pressure can then be decreased to a fraction of the second vacuum pressure, but greater than zero vacuum pressure at 462. In other examples, the pressure can be reduced by the same delta as at 442, e.g., the vacuum pressure can be reduced to a mid-point between the second vacuum pressure and the reduced vacuum pressure at 442. A third reference image is captured at 464.

At 466, the vacuum pressure is increased to a third vacuum pressure that is higher than the second vacuum pressure. A third test image is captured at 468 and the laser is then turned off at 470. The computer with imaging software can use the third test image and the third reference image to determine whether a defect is present as shown at 472. If a defect is detected, the inspection can optionally be stopped at 475. If a defect is not detected, the inspection can continue at 480 by repeating the above steps of increasing the vacuum pressure and capturing a reference speckle image and then decreasing the vacuum pressure to a fraction of the previously increased vacuum pressure and capturing a test speckle image. These steps can be repeated as desired. For example, inspection can continue until a defect is detected or until a predetermined end point is reached. For inspection of composite materials that include microcellular foam, the predetermined end point can be 5 psi because vacuum pressures greater than 5 psi can damage the microcellular foam.

After reading the disclosure herein, one of ordinary skill in the art will understand that the inspection can also be stopped (e.g., at 455, 475) after comparing the reference speckle image to the test speckle image for a number of reasons. For example, the inspection can be stopped at when the applied vacuum pressure reaches a threshold. In the example of declam, inspection can be stopped when the applied vacuum pressure reaches about 5 psi. Alternatively, the inspection can be stopped shortly after the D-Noise plateaus.

Some or all of the disclosed method can be advantageously automated. For example, the increase and decrease of vacuum pressure can be accomplished without an operator by using a computer to control the change in vacuum pressures. This allows inspection to proceed at an accelerated rate so a larger area can be inspected compared to methods reliant on an operator. Automation can further include the determining whether a defect exists by using image processing and pattern recognition software. This can avoid the need for a trained technician to perform the inspection and increase consistency of results.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. For example, steps of the methods have been described as first, second, third, etc. As used herein, these terms refer only to relative order with respect to each other, e.g., first occurs before second. Also, not all process stages may be required to implement a methodology in accordance with one or more aspects or implementations of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

What is claimed is:

1. A shearographic inspection method for detecting defects comprising:
    illuminating a top surface of a test piece with a coherent light;
    capturing a first shearographic image comprising a first speckle pattern, wherein zero vacuum pressure is being applied to the top surface;
    applying a first vacuum pressure to the top surface;
    capturing a second shearographic image comprising a second speckle pattern during the applying of the first vacuum pressure to the top surface;
    using the first speckle pattern and the second speckle pattern to determine whether a defect exists;
    reducing vacuum pressure at the top surface and applying a second vacuum pressure to the top surface, wherein the second vacuum pressure is less than the first vacuum pressure and greater than zero vacuum pressure; and
    capturing a third shearographic image comprising a third speckle pattern during the applying of the second vacuum pressure to the top surface.

2. The method of claim 1 further comprising:
    increasing vacuum pressure at the top surface and applying a third vacuum pressure to the top surface, wherein the third vacuum pressure is greater than the first vacuum pressure;
    capturing a fourth shearographic image comprising a fourth speckle pattern during the applying of the third vacuum pressure; and
    using the third speckle pattern and the fourth speckle pattern to determine whether a defect exists in the test piece.

3. The method of claim 2, further comprising syncing a source of the coherent light to turn off after capturing the second and the fourth shearographic images, and to turn on prior to the reducing of the vacuum pressure to the second vacuum pressure.

4. The method of claim 1, wherein subsequent to capturing the second shearographic image, vacuum pressure remains more than zero at the top surface of the test piece until completion of the shearographic inspection.

5. A nondestructive method for detecting defects in a multi-layered laminate comprising:
    illuminating a top surface of the multi-layered laminate with a coherent light;
    obtaining a first reference speckle image of the top surface of the multi-layered laminate, wherein the top surface is subject to a first vacuum pressure and the first vacuum pressure is 0 or greater during the obtaining of the first reference speckle image;
    applying a second vacuum pressure to the top surface while capturing a first test speckle image of the top surface, wherein the second vacuum pressure is greater than the first vacuum pressure;
    reducing vacuum pressure at the top surface to a third vacuum pressure, wherein the third vacuum pressure is less than the second vacuum pressure and greater than the first vacuum pressure;
    obtaining a second reference speckle image of the top surface while applying the third vacuum pressure to the top surface;
    increasing the vacuum pressure at the top surface to a fourth vacuum pressure, wherein the fourth vacuum pressure is greater than the second vacuum pressure;
    obtaining a second test speckle image of the top surface while applying the fourth vacuum pressure to the top surface; and
    using the second reference speckle image and the second test speckle image to determine whether a defect exists in the multi-layered laminate.

6. The method of claim 5, further comprising:
    reducing vacuum pressure at the top surface to a fifth vacuum pressure, wherein the fifth vacuum pressure is less than the fourth vacuum pressure and greater than the third vacuum pressure;
    obtaining a third reference speckle image of the top surface while applying the fifth vacuum pressure to the top surface;
    increasing vacuum pressure at the top surface to a sixth vacuum pressure, wherein the sixth vacuum pressure is greater than the fourth vacuum pressure;
    obtaining a third test speckle image of the top surface while applying the sixth vacuum pressure to the top surface; and
    using the third reference speckle image and the third test speckle image to determine whether a defect exists between the multi-layered laminate.

7. The method of claim 6, further comprising syncing a coherent light source to turn off the coherent light after obtaining the first and second test speckle images, and to turn on after reducing vacuum pressure to the third and fifth vacuum pressures.

8. The method of claim 7, wherein the third vacuum pressure is a fraction of the second vacuum pressure, and fifth vacuum pressures is the fraction of the fourth vacuum pressure, where the fraction is less than 1.

9. The method of claim 6, wherein the third and fifth vacuum pressures is one of ½, ⅓, or ¼ of the second and fourth vacuum pressures.

10. The method of claim 6, wherein the third vacuum pressure is between the first and second vacuum pressures, and the fifth vacuum pressure is between the third and fourth vacuum pressures by a same difference as the third vacuum pressure is from the first and second vacuum pressures.

11. The method of claim 6, wherein the sixth vacuum pressure is about 5 psi.

12. The method of claim 5, wherein the multi-layered laminate comprises:
a decorative laminate;
a panel skin adhesively bonded to the decorative laminate; and
a core adhesively bonded to the panel skin, wherein the core comprises a honeycomb or a microcellular foam.

13. The method of claim 12, wherein the using of the second reference speckle image and the second test speckle image to determine whether a defect exists comprises determining whether a delamination exists between the decorative laminate and the panel skin.

14. The method of claim 12, wherein the using of the second reference speckle image and the second test speckle image to determine whether a defect exists comprises determining whether a delamination exists between the panel skin and the core.

15. The method of claim 5, wherein the using of the second reference speckle image and the second test speckle image to determine whether a defect exists comprises subtracting the second reference speckle image from the second test speckle image.

16. The method of claim 5, further comprising using the first reference speckle image and the first test speckle image to determine whether a defect exists in the multi-layered laminate.

17. A shearographic inspection system comprising:
a coherent light source configured to provide a coherent beam of light;
one or more optical elements to expand the coherent beam of light and direct the expanded coherent beam of light to illuminate a top surface of a test piece;
a shearography camera to capture speckle images of the illuminated top surface of the test piece;
a loading system configured to increase and decrease a load to the top surface of the test piece in a linearly increasing saw tooth pattern without returning to a zero load state, wherein the loading system is configured to increase and decrease the load at a frequency of 60 Hz or more; and
an image manipulation system to manipulate speckle images of the illuminated top surface of the test piece.

18. The shearographic inspection system of claim 17, wherein the loading system is configured to apply one of a vacuum, heat or mechanical load.

19. The shearographic inspection system of claim 17, wherein the image manipulation system is configured to automatically subtract speckle images, to visually display speckle images that have been subtracted, and to end inspection based on determination a defect is present.

* * * * *